United States Patent [19]

Barry

[11] Patent Number: 5,241,714
[45] Date of Patent: Sep. 7, 1993

[54] SHOWER PERSONAL HYGIENE SYSTEM

[76] Inventor: Paul C. Barry, 4650 W. Oakey #1047, Las Vegas, Nev. 89102

[21] Appl. No.: 736,431

[22] Filed: Jul. 26, 1991

[51] Int. Cl.$^5$ .................. A47K 3/22; A61M 31/00
[52] U.S. Cl. ............................................ 4/605; 4/615; 604/275; 128/66
[58] Field of Search ............... 4/605, 615, 559, 567, 4/420.1, 420.2, 420.3, 420.4, 420.5, 443, 444, 445, 446, 447, 448, 661; 604/39, 275, 279; 128/66

[56] References Cited

U.S. PATENT DOCUMENTS

| | | | |
|---|---|---|---|
| 3,820,532 | 6/1974 | Eberhardt et al. | 128/66 |
| 4,043,337 | 8/1977 | Baugher | 128/66 X |
| 4,242,201 | 12/1980 | Stephens et al. | 4/605 X |
| 4,265,229 | 5/1981 | Rice et al. | 128/66 |
| 4,300,248 | 11/1981 | Dworkin | 4/559 X |
| 4,326,308 | 4/1982 | Silver | 4/444 X |
| 4,398,309 | 8/1983 | Simons | 4/605 |
| 4,553,275 | 11/1985 | Goldstein | 4/605 |
| 4,564,005 | 1/1986 | Marchand et al. | 128/66 |
| 4,793,331 | 12/1988 | Stewart | 4/615 X |
| 4,836,668 | 6/1989 | Christianson | 4/605 X |
| 4,911,704 | 3/1990 | Dixon | 604/279 X |
| 4,979,503 | 12/1990 | Chernack | 128/66 |
| 4,991,569 | 2/1991 | Martin | 4/605 X |
| 5,027,798 | 7/1991 | Primiano | 128/66 |
| 5,070,553 | 12/1991 | Chambers | 4/605 X |

Primary Examiner—William A. Cuchlinski, Jr.
Assistant Examiner—John L. Beres
Attorney, Agent, or Firm—Michael I. Kroll

[57] ABSTRACT

A shower personal hygiene system is provided which consists of a directional fitting connected between a shower neck pipe extending through a wall in a shower stall and a shower head, a hand held attachment and a mechanism for providing fluid communication between the directional fitting and the hand held attachment, so that a person in the shower stall can utilize water under pressure coming from the shower neck pipe to clean various parts of their body.

10 Claims, 2 Drawing Sheets

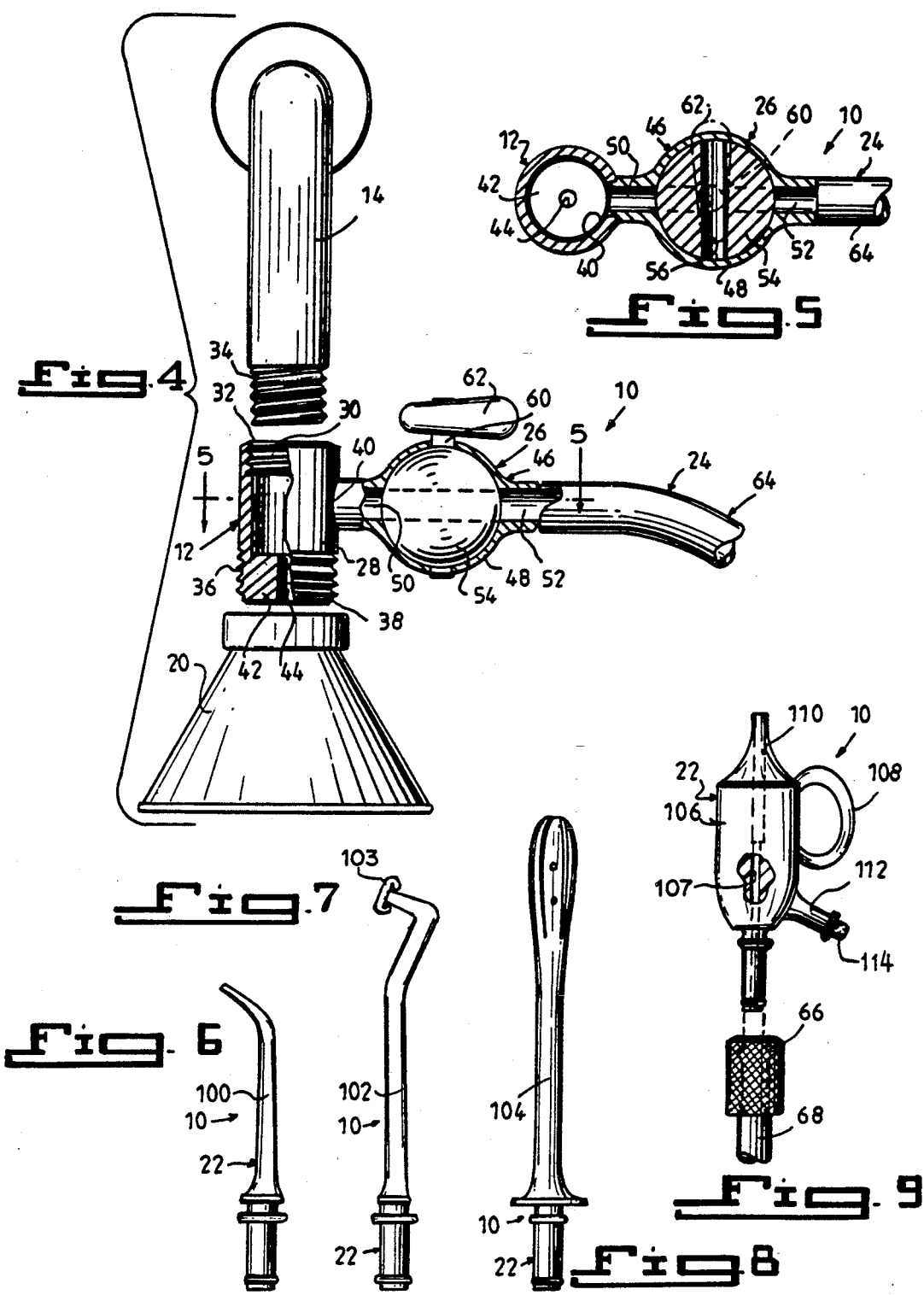

SHOWER PERSONAL HYGIENE SYSTEM

BACKGROUND OF THE INVENTION

1. Field of the Invention

The instant invention relates generally to cleansing devices and more specifically it relates to a shower personal hygiene system.

2. Description of the Prior Art

Numerous cleansing devices have been provided in prior art that are adapted to irrigate cavities in the human anatomy by removing foreign matter therefrom. While these units may be suitable for the particular purpose to which they address, they would not be as suitable for the purposes of the present invention as heretofore described.

SUMMARY OF THE INVENTION

A primary object of the present invention is to provide a shower personal hygiene system that will overcome the shortcomings of the prior art devices.

Another object is to provide a shower personal hygiene system that is fluidly connected between the shower neck pipe and the shower head in a shower stall, so that a person can utilize the shower personal hygiene system while in the shower stall.

An additional object is to provide a shower personal hygiene system in which various attachments can be connected thereto, so that the person in the shower stall can clean and shave with water pressure coming from the shower neck pipe, various parts of their body.

A further object is to provide a shower personal hygiene system that is simple and easy to use.

A still further object is to provide a shower personal hygiene system that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 4 is a front view taken in direction of arrow 4 in FIG. 2, with parts exploded, broken away and in section.

FIG. 5 is a cross sectional view taken along line 5—5 in FIG. 4.

FIG. 6 is a side elevational view of a toothpick member attachment.

FIG. 7 is a side elevational view of a razor member attachment.

FIG. 8 is a side elevational view of a douche member attachment.

FIG. 9 is a side elevational view with parts broken away of an ear cleaner member attachment ready to be inserted into the female quick release snap fitting on the distal end of the elongated flexible tube.

DETAILED DESCRIPTION OF THE PREFERRED EMBODIMENTS

Figure 1:
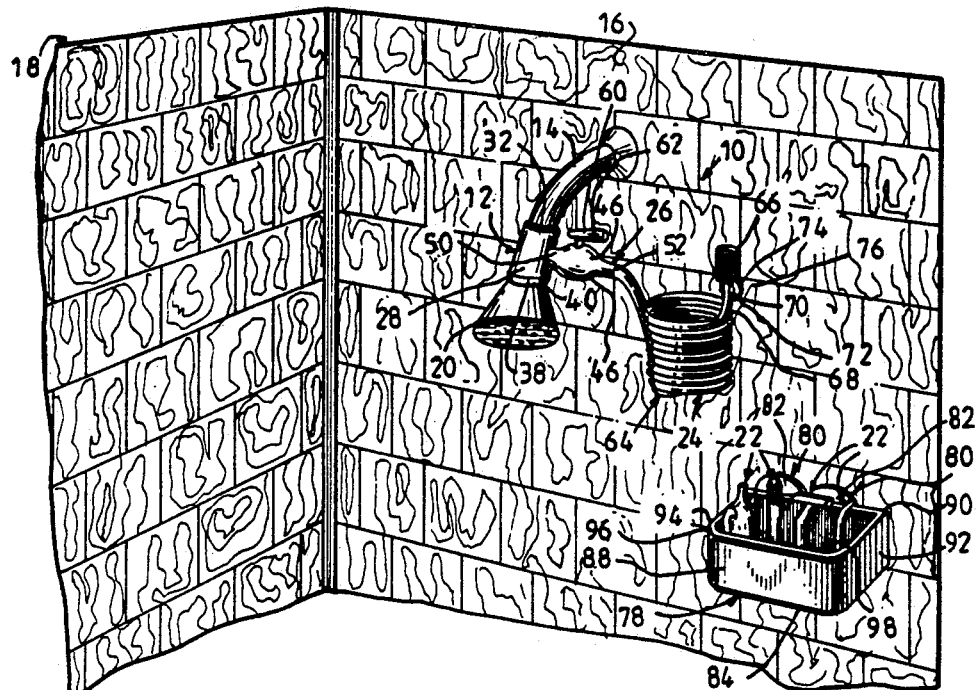
FIG. 1 is a perspective view of the instant invention installed in a shower stall.
Figure 2:
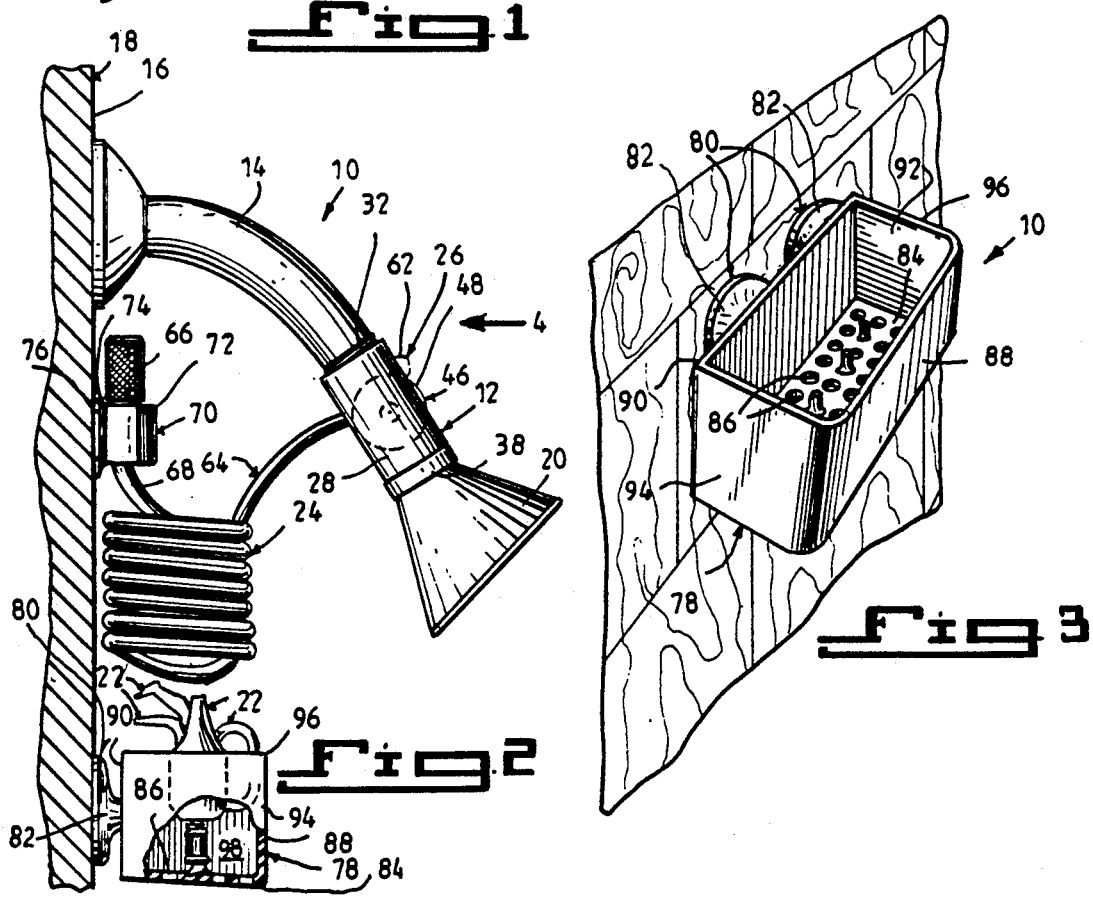
FIG. 2 is a side view of the instant invention shown in FIG. 1, with parts broken away and in section attached to the wall of the shower stall.
Figure 3:
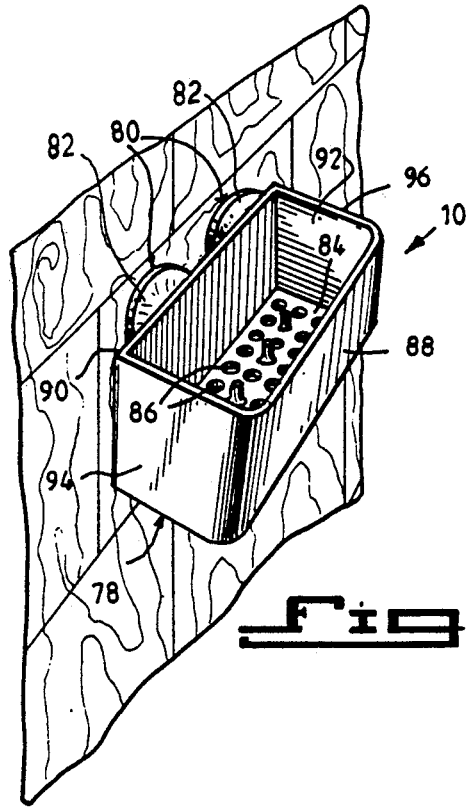
FIG. 3 is a perspective view of just the storage container attached to the wall of the shower stall.

Turning now descriptively to the drawings, in which similar reference characters denote similar elements throughout the several views, the Figures illustrate a shower personal hygiene system 10 which consists of a directional fitting 12 connected between a shower neck pipe 14 extending through a wall 16 in a shower stall 18 and a shower head 20. A hand held attachment 22 is also provided with a fluid communication mechanism 24 located between the directional fitting 12 and the hand held attachment 22, so that a person in the shower stall 18 can utilize water under pressure coming from the shower neck pipe 14 to clean various parts of their body.

A mechanism 26 is located between the directional fitting 12 and the fluid communication mechanism 24 for regulating the flow of the water therethrough.

The directional fitting 12 includes a hollow cylindrical sleeve 28 having internal thread 30 at a first end 32 to engage with external threads 34 on the shower neck pipe 14. External threads 36 are at a second end 38 to engage with the internal threads (not shown), in the shower head 20. A transverse aperture 40 is between the first end 32 and the second end 38 thereof, so that the regulating mechanism 26 can be attached thereto.

The hollow cylindrical sleeve 28 further includes an enclosure 42 having a small orifice 44 located at the second end 38 thereof to supply uniform water pressure to the shower head 20 and the regulating mechanism 26. The regulating mechanism 26 is an on/off manually operated valve 46 and includes a housing 48 having an inlet port 50 fluidly connected to the transverse aperture 40 in the hollow cylindrical sleeve 28 of the directional fitting 12 and an outlet port 52 fluidly connected to the fluid communication mechanism 24. A ball 54 having a longitudinal bore 56 therethrough, is rotatably mounted within the housing 48. A spindle 60 extends upwardly form the ball 54 through the housing 48. A handle 62 is affixed to the top of the spindle 60, so as to rotate the ball 54 causing the longitudinal bore 56 to align up with the inlet and outlet ports 50 and 52 of the housing 48 to regulate the flow of the water therethrough.

The fluid communication mechanism 24 is an elongated flexible tube 64 extending between the outlet port 52 of the housing 48 of the on/off manually operated valve 46 and the hand held attachment 22. A female quick release snap fitting 66 is located on the distal end 68 of the elongated flexible tube 64, so that the hand held attachment 22 can be easily connected and disconnected therefrom.

A bracket 70 is attached to the wall 16 of the shower stall 18, so that the distal end 68 of the elongated flexible tube 64 with the female quick release snap fitting 66 can be held thereto when not in use. The bracket 70 includes a clamp member 72 to engage the distal end 68 of the elongated flexible tube 64 and a mechanism 74 for attaching the clamp member 70 to the wall 16 of the shower stall 18. The attaching mechanism 74 is a suction cup 76 mounted to the back of the clamp member 72, whereby the suction cup 76 can stick to the wall 16 of the shower stall 18.

A storage container 78 is for holding the hand held attachment 22 therein, when the hand held attachment 22 is removed from the female quick release snap fitting 66. A mechanism 80 is for attaching the storage container 78 to the wall 16 of the shower stall 18 and is at least one suction cup 82 mounted to the back of the storage container 78, whereby the at least one suction cup 82 can stick to the wall 16 of the shower stall 18.

The storage container 78 includes a floor 84 having a plurality of perforations 86 therethrough, so that when the hand held attachment 22 is placed therein when not in use, the perforations 86 in the floor 84 will allow for water drainage from the hand held attachment 22. The storage container further includes a front wall 88, a rear wall 90, a right side wall 92, a left side wall 94 and an open top area 96, so as to define a chamber 98 with the perforated floor 84, to place and store the hand held attachment 22 therein when not in use.

As best seen in FIG. 6, the hand held attachment 22 is a curved toothpick member 100, for cleaning the teeth and gums of the person with the pressurized water exiting therefrom. As best seen in FIG. 7, the hand held attachment 22 is a razor member 102 having a replaceable razor blade 103, for shaving hair from the skin of the person, while the pressurized water exits therefrom. As best seen in FIG. 8, the hand held attachment 22 is a straight penis-shaped douche member 104, for cleaning the private parts of a female person with the pressurized water exiting therefrom. As best seen in FIG. 9, the hand held attachment 22 is an ear cleaner member 106 having an internal orifice 107, for cleaning the ears of a person, with pressurized water exiting therefrom.

The ear cleaner member 106 includes a finger ring holder 108 extending from the side thereof, to assist the person in griping onto the ear cleaner member 106. A nozzle 110 extends from the top thereof to allow the pressurized water to exit therefrom into the ear. An outer ear cleaning stanchion 112 extends at an angle from the side thereof below the finger ring holder 108. A sponge tip 114 is for the outer ear cleaning stanchion 112, which can be removed and replaced when needed.

The shower personal hygiene system 10, as shown in the drawings and described above, is directly connected to the shower neck pipe 14. The system 10 can also come directly off other types of plumbing fixtures, such as a tub or sink faucet and a no-fog shower mirror directional chamber.

LIST OF REFERENCE NUMBERS

10: shower personal hygiene system
12: directional fitting
14: shower neck pipe
16: wall
18: shower stall
20: shower head
22: hand held attachment
24: fluid communication mechanism
26: regulating mechanism
28: hollow cylindrical sleeve
30: internal threads in 28
32: first end on 28
35: external threads on 14
36: external threads on 28
38: second end on 28
40: transverse aperture in 28
42: enclosure at 38
44: small orifice in 42
46: on/off manually operated valve
48: housing
50: inlet port in 48
52: outlet port in 48
54: ball
56: longitudinal bore in 54
60: spindle
62: handle on 60
64: elongated flexible tube
66: female quick release snap fitting
68: distal end of 64
70: bracket
72: clamp member of 70
74: attaching mechanism for 72
76: suction cup for 74
78: storage container
80: attaching mechanism for 78
82: suction cup for 80
84: floor in 78
86: perforations in 84
88: front wall in 78
90: rear wall in 78
92: right side wall in 78
94: left side wall in 78
96: open top area in 78
98: chamber in 78
100: curved toothpick member for 22
102: razor member for 22
103: replaceable razor blade
104: straight penis-shaped douche member for 22
106: ear cleaning member for 22
107: internal orifice in 106
108: finger ring holder on 106
110: nozzle on 106
112: outer ear cleaning stanchion on 106
114: sponge tip for 112

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A shower personal hygiene system which comprises:
    a) a directional fitting connected between a shower neck pipe extending through a wall in a shower stall and a shower head, said directional fitting includes a hollow cylindrical sleeve having internal threads at a first end to engage with the external threads on the shower neck pipe, external threads at a second end to engage with the internal threads in the shower head and a transverse aperture between the first end and the second end thereof, so that said regulating means can be attached thereto, said hollow cylindrical sleeve further includes an enclosure having a small orifice located at the second end thereof to supply uniform water pressure to the shower head and said regulating means;

b) a hand held attachment;

c) means for providing fluid communication between said directional fitting and said hand held attachment, so that a person in the shower stall can utilize water under pressure coming from the shower neck pipe to clean various parts of their body said fluid communication means is an elongated flexible tube extending between the outlet port of said housing of said on/off manually operated valve and said hand held attachment;

d) means located between said directional fitting and said fluid communication means, for regulating the flow of the water therethrough, said regulating means is an on/off manually operated valve, said on/off manually operated valve includes a housing having an inlet port fluidly connected to the transverse aperture in said hollow cylindrical sleeve of said directional fitting and an outlet port fluidly connected to said fluid communication means, a ball having a longitudinal bore therethrough, said ball rotatably mounted within said housing, a spindle extending upwardly from said ball through said housing, a handle affixed to the top of said spindle, so as to rotate said ball causing the longitudinal bore to align up with the inlet and outlet ports of said housing to regulate the flow of the water therethrough;

e) a female quick release snap fitting located on distal end of said elongated flexible tube, so that said hand held attachment can be easily connected and disconnected therefrom; and f) a bracket attached to the wall of the shower stall, so that the distal end of said elongated flexible tube with said female quick release snap fitting can be held thereto when not in use, said bracket includes a clamp member to engage the distal end of said elongated flexible tube, means for attaching said clamp member to the wall of the shower stall, said attaching means is a suction cup mounted to the back of said clamp member, whereby said suction cup can stick to the wall of the shower stall.

2. A shower personal hygiene system as recited in claim 1, further including:

a) a storage container for holding said hand held attachment therein, when said hand held attachment is removed from said female quick release snap fitting; and b) means for attaching said storage container to the wall of the shower stall.

3. A shower personal hygiene system as recited in claim 2, wherein said attaching means is at least one suction cup mounted to the back of said storage container, whereby said at least one suction cup can stick to the wall of the shower stall.

4. A shower personal hygiene system as recited in claim 3, wherein said storage container includes a floor having a plurality of perforations therethrough, so that when said hand held attachment is placed therein when not in use, the perforations in said floor will allow for water drainage from said hand held attachment.

5. A shower personal hygiene system as recited in claim 4, wherein said storage container further includes:

a) a front wall;
b) a rear wall;
c) a right side wall;
d) a left side wall; and
e) an open top area, so as to define a chamber with said perforated floor, to place and store said hand held attachment therein when not in use.

6. A shower personal hygiene system as recited in claim 5, wherein said hand held attachment is a curved toothpick member for cleaning the teeth and gums of the person with the pressurized water exiting therefrom.

7. A shower personal hygiene system as recited in claim 5, wherein said hand held attachment is a razor member having a replaceable razor blade, for shaving hair from the skin of the person, while the pressurized water exits therefrom.

8. A shower personal hygiene system as recited in claim 5, wherein said hand held attachment is a straight penis-shaped douche member, for cleaning the private parts of a female person with the pressurized water exiting therefrom.

9. A shower personal hygiene system as recited in claim 5, wherein said hand held attachment is an ear cleaner member having an internal orifice, for cleaning the ears of a person, with pressurized water exiting therefrom.

10. A shower personal hygiene system as recited in claim 9, wherein said ear cleaner member includes:

a) a finger ring holder extending from the side thereof to assist the person in gripping onto said ear cleaner member;
b) a nozzle extending from the top thereof to allow the pressurized water to exit therefrom into the ear;
c) an outer ear cleaning stanchion extending at an angle from the side thereof below said finger ring holder; and
d) a sponge tip for said outer ear cleaning stanchion which can be removed and replaced when needed.

* * * * *